United States Patent [19]

Engel

[11] 4,423,255
[45] Dec. 27, 1983

[54] (+)-4-SUBSTITUTED-2-INDANOLS

[75] Inventor: John F. Engel, Medina, N.Y.

[73] Assignee: FMC Corporation, Philadelphia, Pa.

[21] Appl. No.: 379,390

[22] Filed: May 17, 1982

Related U.S. Application Data

[60] Division of Ser. No. 221,656, Dec. 31, 1980, and a continuation-in-part of Ser. No. 42,372, May 24, 1979, which is a continuation of Ser. No. 927,198, Jul. 24, 1978, and Ser. No. 870,973, Jan. 20, 1978.

[51] Int. Cl.³ .............................................. C07C 35/32
[52] U.S. Cl. ..................................................... 568/808
[58] Field of Search ................ 568/808, 809; 424/304, 424/305

[56] References Cited

U.S. PATENT DOCUMENTS

| | | | |
|---|---|---|---|
| 3,439,046 | 4/1969 | Brown | 568/808 |
| 3,647,857 | 3/1972 | Morgan | 568/808 |
| 3,673,215 | 6/1972 | Vollrath et al. | 568/808 |
| 4,024,163 | 5/1977 | Elliott et al. | 260/347 |
| 4,157,397 | 6/1979 | Engel | 424/274 |
| 4,160,842 | 7/1979 | Engel | 424/274 |
| 4,183,948 | 1/1980 | Huff | 424/304 |
| 4,208,352 | 6/1980 | Huff | 424/304 |
| 4,263,319 | 4/1981 | Gardner | 568/808 |
| 4,333,950 | 6/1982 | Engel | 424/305 |
| 4,362,744 | 12/1982 | Plummer | 568/808 |

OTHER PUBLICATIONS

*Synthetic Pyrethroids*, ACS Symposium Series, No. 42, M. Elliott, Ed., American Chemical Society, Washington, D.C., 1977, Chapter 1.
*Synthetic Pyrethroids*, ibid, Chapter 4.
R. E. Burt et al., *Pesticide Science*, 5, 791, (1974).
H. C. Brown, *Hydroboration*, W. A. Benjamin, Inc., New York, 1962, Chapter 14.
P. A. Marshall et al., *Aust. J. Chem.*, 32, 1251, (1979).
Nakada et al., *Agric. Biol. Chem.*, 42, 1357, (1978).

*Primary Examiner*—Werren B. Lone
*Attorney, Agent, or Firm*—Robert M. Kennedy; H. Robinson Ertelt; Robert L. Andersen

[57] ABSTRACT

Novel compounds of the formula

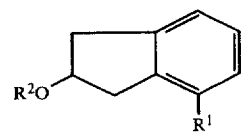

are disclosed in which $R^1$ is a phenyl, phenoxy, phenylthio, benzyl or heterocyclic radical which may be substituted, $R^2$ is hydrogen, a substituted-vinylcyclopropanecarbonyl group, a tetramethylcyclopropanecarbonyl group, or a 1-(substituted-phenyl)-2-methylpropylcarbonyl group, and the isomer of S configuration at C-2 of the indanyl ring is present in an enantiomeric excess over the isomer of R configuration. Also disclosed is a method for preparing the optically active alcohols. The compounds wherein $R^2$ is other than hydrogen are insecticides.

3 Claims, No Drawings

(+)-4-SUBSTITUTED-2-INDANOLS

This application is a division, of application Ser. No. 221,656, filed Dec. 31, 1980, and a continuation in part of U.S. Ser. No. 042,372, filed May 24, 1979, which itself is a continuing application of U.S. Ser. Nos. 927,198 filed July 24, 1978, and 870,973, filed Jan. 20, 1978, the disclosures of all of which are incorporated herein by reference.

The invention is directed to an optically active alcohol, to a method for preparing the alcohol, to insecticidal or acaricidal pyrethroid esters of the alcohol, and to an insecticidal or acaricidal method and composition. In particular, the invention relates to (+)-4-substituted-2-indanol; its preparation, utility, and insecticidal and acaricidal derivatives.

Pyrethrins, naturally occurring extracts of chrysanthemum flowers, have long been of interest as insecticides. Since elucidation of the structures of these compounds, synthesis efforts have been directed toward preparation of related compounds having enhanced insecticidal activity and improved stability toward air and light. Since a prerequisite for insecticidal activity of pyrethroids is the presence in one molecule of an appropriate acid moiety and an appropriate alcohol moiety, research in the art has been directed toward novel acid and/or alcohol radicals. Noteworthy advances in the area of alcohol research were the discovery of 5-benzyl-3-furylmethyl alcohol, then of the more photostable 3-phenoxybenzyl alcohol (see *Synthetic Pyrethroids*, ACS Symposium Series, No. 42, M. Elliott, Ed., American Chemical Society, Washington, D.C. 1977, Chapter 1). Similarly significant advances have been made in pyrethroid acid research. The commercial insecticide permethrin, the common name for 3-phenoxyphenyl-methyl 3-(2,2-dichloroethenyl)-2,2-dimethylcyclopropanecarboxylate, exemplifies use of both newer acid and alcohol moieties in a single compound.

The parent case of the present application discloses, inter alia, a series of novel 4-substituted-2-indanyl alcohols as pyrethroid insecticide intermediates, and a method for producing them. The disclosed method employs racemic starting materials and achiral synthesis techniques, and the indanols thereby produced are racemic materials, each being comprised of equal amounts of the 2S or dextrorotatory isomer and the 2R or levorotatory isomer. The present invention pertains to a chiral synthesis method for producing 4-substituted-2-indanyl alcohols, which provides accessibility of an optically active form of the indanols wherein the dextrorotatory, 2S, isomer is present in an enantiomeric excess over the 2R isomer of at least 25%. Pyrethroid esters of these (+)-4-substituted-2-indanols generally have greatly enhanced insecticidal properties over the corresponding esters having the racemic alcohol moiety.

In this application, the term "lower" as applied to an aliphatic hydrocarbon group means having 1 to 6 carbon atoms, preferably 1 to 4 carbon atoms. The term "halo" or "halogen" means bromine, chlorine or fluorine. The term "haloalkyl" means an alkyl group of 1 to 3 carbon atoms substituted with 1 or more halogen atoms. The term "insecticide" is used in its broadest sense and includes compounds possessing activity against true insects, acarids, and other household, veterinary or crop pests of the phylum Arthropoda. "Enantiomeric excess" or "EE" is the percent excess of one enantiomer over the other in a mixture containing two enantiomers of a compound, in accordance with the formula % $EE = (X-Y)/(X+Y) \cdot 100$ where X is the concentration of the more abundant enantiomer in the mixture, and Y is the concentration of the less abundant enantiomer. An enantiomeric excess of 100% means that for all practical purposes only one of the two enantiomers is present. The term "dextrorotatory" or the designation "(+)" when used to denote optical rotation of a 4-substituted-2-indanol refers to the optical rotation attributable to the asymmetric center at C-2 of the indane ring, and means that the dextrorotatory isomer, which has the S absolute configuration at C-2, is present in an enantiomeric excess. These definitions are applicable throughout the specification and claims except where a contrary meaning is clearly indicated.

The 4-substituted-2-indanyl compounds of this invention have the general formula

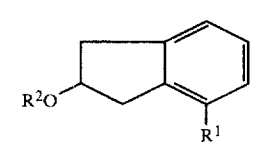

in which $R^1$ is a phenyl, phenoxy, phenylthio, benzyl or heterocyclic radical which may be substituted with halogen, lower alkyl, halo(lower)alkyl, lower alkoxy, lower alkylthio, cyano or nitro, particularly halogen or lower alkyl; $R^2$ is a hydrogen, 2,2,3,3-tetramethylcyclopropylcarbonyl, 1-(substituted-phenyl)-2-methylpropyl-1-carbonyl, particularly 1-(4-chlorophenyl)-2-methylpropyl-1-carbonyl, or a group of the formula:

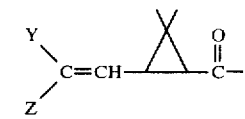

wherein Y and Z, the same or different, are hydrogen, halogen, lower alkyl, perhalo(lower)alkyl, phenyl which may be substituted with halogen or lower alkyl, or phenylthio which may be substituted with halogen or lower alkyl, with the proviso that one of Y and Z is other than hydrogen; and the isomer of S configuration at C-2 of the indanyl ring is present in an enantiomeric excess of at least 25%, preferably at least 60%, over the isomer of R configuration at C-2 of the indanyl ring.

When $R^1$ is a heterocyclic radical, it is advantageously a 5 or 6 membered ring consisting of carbon and 1 to 3 ring members selected from oxygen, nitrogen, and sulfur. Suitable heterocyclic radicals include furanyl, thienyl, pyridyl, pyrimidyl, oxazolyl, pyrrolyl, isoxazolyl, thiazolyl, and isothiazolyl.

The alcohols of this invention are the compounds of formula I in which $R^2$ is hydrogen. Alcohols of especial interest are those wherein $R^1$ is phenyl which may be substituted with halogen or lower alkyl. For reasons of convenience, ready accessibility, and economy of cost, $R^1$ will frequently be unsubstituted phenyl. Theoretically, for maximum insecticidal activity of the end product pyrethroid esters, the alcohol should generally consist primarily of the dextrorotatory, 2S, isomer. In actual practice, however, a somewhat less than 100% EE of this isomer will generally provide a satisfactory increase in the level of insecticidal activity over the corresponding racemic alcohol containing material, and in certain situations may even give control comparable to or greater than that afforded by use of an equal amount of the corresponding product having a higher enantiomeric excess. As a general rule, however, the enantiomeric excess of the 2S isomer should be at least 25%, preferably at least 60%. The 2S configuration is that depicted in the following structural formula:

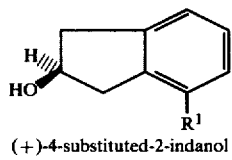

(+)-4-substituted-2-indanol

Particularly useful insecticides of the present invention are the cyclopropanecarboxylates in which one of Y and Z is halogen, such as chlorine or bromine, and the other, the same or different, is halogen or a perhaloalkyl group such as trihalomethyl, especially trifluoromethyl; $R^1$ is phenyl which may be substituted with halogen or lower alkyl, preferably unsubstituted phenyl; and the isomer of S configuration at C-2 of the indanyl ring is present in an enantiomeric excess of at least 25%, preferably at least 60%, over the isomer of R configuration.

The cyclopropanecarboxylates having the acid residue of formula II have cis and trans isomeric forms, i.e., the carboxy and the substituted vinyl groups at the 1 and 3 positions of the cyclopropane ring are either cis or trans with respect to each other. Preparation of these compounds will usually yield a mixture of the cis and trans isomers, designated herein as cis,trans, in which the ratio of cis to trans may vary over a wide range. In the cyclopropanecarboxylate art it is known there may be substantial differences in the level of insecticidal activity of the cis and trans isomers. In general, as between the cis and trans isomer of a given cyclopropanecarboxylate of the present invention, the cis isomer is usually more active than the trans and also more active than the cis,trans mixture. Also, the cis isomer having the R configuration at C-1 of the cyclopropane ring is usually more active than the corresponding cis isomer with the S configuration and also more active than the 1R,S mixture. For purposes of this application the designations cis and trans are assigned in accordance with P. E. Burt, et al., Pestic. Sci., 5 791–799 (1974).

The compounds where Y is different from Z may also exist as E or Z isomers or as mixtures of E and Z isomers, designated E,Z, depending upon the spatial relationship of substituents on the α-carbon of the vinyl group to those on the β-carbon of the vinyl group. Differences in activity may also occur with respect to these E and Z isomers.

Unless a contrary intent is specifically expressed, this invention embodies and includes both cis and trans isomeric forms of the claimed compounds as well as mixtures thereof wherein the cis to trans ratio is within the range of 0:100 to 100:0. Similarly, the individual E and Z isomers, as well as the mixtures, are contemplated by and within the scope of the invention. The various enantiomers of the claimed compounds and mixtures of them are also included within the scope of the invention.

The process aspect of the present invention relates to a method for producing a 4-substituted-2-indanol of the formula

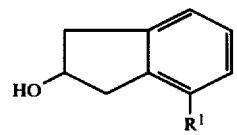

Ia wherein $R^1$ is defined as above, and the isomer of S configuration at C-2 of the indanyl ring is present in an enantiomeric excess of at least 25% over the isomer of R configuration.

The process comprises the steps of (i) bringing together under hydroboration conditions (+)-α-pinene and borane, about 2 to 4 moles of (+)-α-pinene being used for each mole of borane employed, to produce an intermediate borane derivative having at least one active hydrogen atom, (ii) contacting under hydroboration conditions the intermediate borane derivative with a 7-substituted-1H-indene of the formula

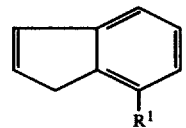

wherein $R^1$ is as defined above, so as to cause the indene to undergo a hydroboration reaction, and (iii) contacting the product of step (ii) with an oxidizing agent to produce the 4-substituted-2-indanol of formula Ia.

The present process is illustrated in the following schema:

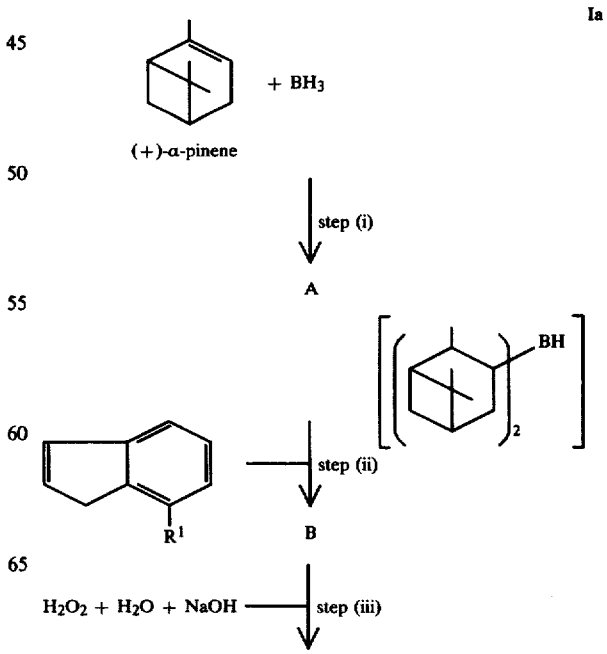

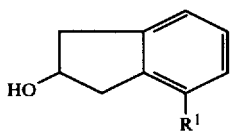

Hydroboration of (+)-α-pinene, and use of the reaction product in an asymmetric hydroboration of certain alkenes to produce optically active alcohols is discussed by H. C. Brown in *Hydroboration*, W. A. Benjamin, Inc., New York, 1962, chapter 14. Brown indicates that the hydroboration of (+)-α-pinene in diethyleneglycol dimethyl ether, or in tetrahydrofuran when an excess of α-pinene is used, proceeds to the dialkylborane stage to form diisopinocamphenylborane.

In the present case, no attempt was made to identify the product of either step (i) or step (ii). However, in view of the Brown reference, it is likely that the step (i) product, particularly where (+)-α-pinene is employed in excess, consists predominantly of diisopinocampheylborane, depicted in monomeric form in brackets in the schema above as intermediate A. The corresponding monoalkyl and trialkyl derivatives of borane may also be components of the reaction mixture, but both are expected to be present, if at all, in small quantities only. The monoalkyl derivative has two active hydrogen atoms available for further hydroboration, and is itself a suitable reactant for the step (ii) hydroboration reaction. The trialkyl derivative, however, would be unreactive in step (ii).

The process is preferably and conveniently conducted without isolation of the intermediates, A and B in the schema above. The hydroboration conditions of steps (i) and (ii) are those typically used in the art for hydroboration reactions, and include use of an ether solvent and a low reaction temperature.

The ether solvent is advantageously water miscible to facilitate the step (iii) oxidation in which, in the preferred mode, water or water based solutions are mixed with the step (ii) reaction mixture containing intermediate B. Such ethers include 1,2-dimethoxyethane, diethyleneglycol dimethyl ether, dioxane, and tetrahydrofuran.

A temperature in the range of about −50° to 35° C. during the hydroboration steps is generally acceptable. However, it is desirable that the temperature be no higher than about 10° or 15° C. during step (i) and the initial, reactive, phase of step (ii). Advantageously, the temperature should be maintained in the range of about −10° C. to 15° C. until the step (ii) reaction has gone almost to completion. Then, it is useful to raise the temperature to about 35° C., or even higher, for the duration of the reaction period.

In step (i), about 2.0 to 4.0 moles, preferably about 2.0 to 2.5 moles, of (+)-α-pinene are employed for each mole of borane reactant used. It is desirable that the indene in step (ii) be employed in from about one third to two thirds, preferably about one half, the molar quantity of borane used in step (i).

The step (iii) oxidation may be conducted under conditions generally employed in the art for similar oxidations of hydroborated intermediates. Preferably, the oxidizing agent is hydrogen peroxide, and the reaction is conducted in the presence of water and a base, for example, sodium hydroxide or potassium hydroxide.

The 4-substituted-2-indanol obtained in step (iii) will require further purification if a substantially pure product is desired. The crude product contains in addition to the desired 2-indanol a substantial quantity of the corresponding 4-substituted-1-indanol, and possibly other contaminants such as unreacted 7-substituted-1H-indene or α-pinene. The 1-indanol is produced as a result of a side reaction in step (ii) wherein the boron atom of the hydroborating species adds to the C-3 carbon, rather than the C-2 carbon, of the 7-substituted-1H-indene substrate. The ratio of 2-indanol to 1-indanol in the crude product is generally not lower than about 3:1, and may be as high as about 4:1 or 5:1.

The desired 4-substituted-2-indanol can be substantially separated from the crude or partially purified product from step (iii) by separation techniques known in the art. However, the physical properties of the 1-indanol contaminant will be similar to those of the 2-indanol, and a separation based only on differences in physical properties will be somewhat inefficient.

An effective and preferred method for recovering the 4-substituted-2-indanol from the crude or partially purified product from step (iii) is based in part on the difference in chemical properties of the two indanol components of the product mixture. In this method, the mixture is subjected to dehydration conditions that are sufficiently severe to effect decomposition of the more labile 1-indanol, yet are mild enough not to substantially affect the desired 2-indanol. Dehydration of the 4-substituted-1-indanol results in reformation of 7-substituted-1H-indene, the substrate of step (ii) and possibly already a contaminant from that source. The 2-indanol may then be separated from the non-polar indene and other possible components by conventional separation techniques based on differences in physical properties such as column chromatography. The dehydration is conducted in the presence of a dehydrating agent, preferably p-toluenesulfonic acid, and a solvent at an elevated temperature, for example toluene at reflux temperature. This method is described in detail in Example 2 for 4-phenyl-2-indanol.

A second method for effectively separating or recovering the desired 2-indanol from the crude or partially purified product from step (iii) involves converting the two indanol components into derivatives that are readily separable by chromatography or other means. For example, the two indanols can be converted into esters such as acetates or other alkanoates by treating the product mixture with a carboxylic acid halide under esterification conditions. The resulting ester of the 2-indanol can then be separated by conventional means of separation such as chromatography, and hydrolyzed to recover the 4-substituted-2-indanol substantially free of the 1-indanol and other contaminants. This method is described in detail in Example 1 for 4-phenyl-2-indanol.

The 4-substituted-2-indanol produced by the present process will have an enantiomeric excess somewhat less than 100%, but at least 25%. In most cases the EE will be well above 25%, generally in the range of about 40% to 60%. Where the 2-indanol is a solid or crystalline material, it is possible merely by washing the solid product with an organic solvent to increase the enantiomeric excess further to an EE generally in the range of about 60% to 100%. The solvent is preferably an aromatic hydrocarbon such as benzene, toluene, chlorobenzene, or o-, m-, or p xylene, or mixtures thereof. The type and amount of solvent used should be such to dissolve the 2-indanol partially but not completely. Since the 2S and 2R isomers of the 4-substituted-2-indanol are enantiomers, they will be soluble in equal amounts in the solvent. So long as both isomers are present in the sample being washed, the solvent will dissolve an equimolar amount of each isomer thereby further enriching the undissolved material with the originally more abundant S isomer. This method of isomer enrichment or refinement is described in Example 3 for 4-phenyl-2-indanol which had previously been purified and crystallized. The washing was accomplished with toluene at room temperature.

The insecticidal compounds having the acid residue of formula II may be prepared from alkanoates of the formula

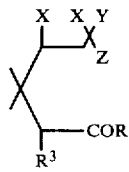
III in which Y and Z are defined as above; R is lower alkoxy, such as methoxy or ethoxy, or a 4-substituted-2-indanyloxy moiety from an alcohol of formula I; $R^3$ is hydrogen, lower alkylcarbonyl, lower alkoxycarbonyl, or cyano, preferably hydrogen; and X is chloro or bromo. Example 4 illustrates a method for preparation of the alkanoate intermediates of formula III whereby a lower alkyl 3,3-dimethyl-4-pentenoate is allowed to react with a compound of the formula $X_2C(Y)(Z)$ wherein X, Y, and Z are as defined above.

Dehydrohalogenation of the compound of formula III followed, if necessary, by hydrolysis of the ester and, also if necessary, halogenation of the resulting carboxyl group gives a compound of the formula

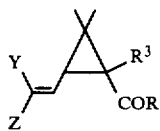
IV in which R is lower alkoxy, hydroxy, halogen, or a 4-substituted-2-indanyloxy moiety from an alcohol of formula I, and Y, Z and $R^3$ are as defined above. The dehydrohalogenation reaction may proceed through one or more intermediates of the formulas:

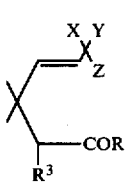  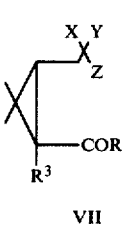
V  VI  VII and may be conducted in a single step by elimination of 2 equivalents of hydrogen halide, HX, to give a compound of formula VI directly, or in multiple steps under conditions allowing a sequential elimination of the 2 equivalents of HX in separate reactions. These intermediates or mixtures thereof may be recovered if desired. The compound of formula IV wherein $R^3$ is a hydrogen atom, R is a hydroxy group, and each of Y and Z is a bromine atom can also be prepared from the corresponding compound wherein each of Y and Z is a chlorine atom or one of Y and Z is a chlorine atom and the other is a bromine atom by treatment of the compound bearing the chlorine atom or atoms with aluminum in the presence of hydrogen bromide gas and dibromomethane. This method is exemplified in Example 9.

The compound of formula IV is converted to the compound of formula I by methods known to the art, for example, by removing $R^3$ (if other than hydrogen) and, where R is lower alkoxy, hydroxy, or halogen, esterifying or transesterifying with a 4-substituted-2-indanol of formula I ($R^2$ is hydrogen).

The examples which follow illustrate preparation of the insecticidal compounds and novel alcohol intermediates therefor in accordance with the general method described above. In the examples all temperatures are in degrees centigrade, all pressures are in mm Hg, and reduced pressure for concentrations of liquid was produced by a water aspirator unless otherwise specified. The enantiomeric excess percentages were calculated from peak heights obtained from an nmr analysis of the acetate derivatives of the 4-substituted-2-indanol, in the presence of a chiral shift reagent. The shift reagent used was tris-[3-(heptafluoropropylhydroxymethylene)-d-camphorato], europium (III) derivative, [Eu(hfc)₃]. The heights of the peaks for the methyl protons from the acetyl groups were used as the concentration figures in the formula % EE=(X−Y)/(X+Y)·100 where X is the concentration of the S isomer, and Y is the concentration of the R isomer. It is difficult to accurately determine EE's greater than about 95% by the chiral shift reagent method. Therefore, values in the range of 95% to 100% are expressed simply as being ≧95%.

Examples 1 and 2 describe the preparation of the alcohols, compounds of formula I wherein $R^2$ is hydrogen. In Example 1, the esterification method for obtaining substantially pure product is described in detail, whereas in Example 2, the dehydration method is described. Example 3 describes the isomer enrichment or refinement step wherein the 4-substituted-2-indanol is further enriched with the S isomer by washing the substantially pure 2-indanol with an organic solvent.

EXAMPLE 1

Synthesis of (+)-4-Phenyl-2-Indanol

A. Hydroboration of 7-phenyl-1H-indene

Under a dry nitrogen atmosphere, a solution of 5.45 g (0.04 mole) of (+)-α-pinene in 15 ml of tetrahydrofuran was stirred and cooled to 0° C. Twenty ml of a 1 M solution of boranetetrahydrofuran complex (0.02 mole) was added slowly, and the reaction mixture was stirred at 0° C. for 1 hour. To this was added dropwise a solution of 3.28 g (0.017 mole) of 7-phenyl-1H-indene in 15 ml of tetrahydrofuran. The reaction mixture was stirred at 0° C. for 2.5 hours, then at room temperature for 2 hours. The mixture was cooled to 0° C., and 6.9 ml of water, 10.3 ml of a 3 N sodium hydroxide solution, and finally 10.3 ml of 30% hydrogen peroxide were added in sequence slowly. The mixture was stirred at room temperature for two days, then poured into water, and extracted with two 100 ml portions of diethyl ether. The ether extracts were washed with 100 ml of water, dried with anhydrous sodium sulfate, filtered, and the filtrate concentrated to give an oil. The oil was distilled using a Kugelrohr distillation apparatus (95° C./2.5 mm) to leave 2.62 g of an oily pot residue. The nmr spectrum of the oily residue indicated a 3:1 ratio of 4-phenyl-2-indanol to 4-phenyl-1-indanol (99% purity by gas chromatography).

B. Separation of 4-phenyl-2-indanol

Esterification Method

A stirred solution of 2.46 g (0.0117 mole) of the 3:1 mixture of 4-phenyl-2-indanol and 4-phenyl-1-indanol from above and 1.03 g (0.013 mole) of pyridine in 15 ml of toluene was cooled to 5° C. A solution of 0.94 g (0.012 mole) of acetyl chloride in 6 ml of toluene was added dropwise, and the mixture was stirred at room temperature for 16 hours. The mixture was filtered, and the filtrate concentrated under reduced pressure to give 2.57 g of an oily residue. The oil was subjected to column chromatography on silica gel, eluting first with hexane, then with 98:2 hexane/ethyl acetate. Appropriate fractions were combined to give 0.34 g of the 2-yl acetate and 1.53 g of a mixture of 2-yl and 1-yl acetates. Rechromatography of the 1.53 g mixture, eluting with hexane, 99:1 hexane/ethyl acetate, and finally 98:2 hexane/ethyl acetate gave an additional 1.04 g of the 2-yl acetate. The nmr spectrum was consistent with the proposed structure. In a similar preparation of 4-phenyl-2-indanyl acetate, the product was analyzed by nmr spectroscopy using a shift reagent, Eu(hfc)$_3$. The results indicated a 50% enantiomeric excess of the dextrorotatory isomer.

A mixture of 1.22 g (0.0048 mole) of 4-phenyl-2-indanyl acetate, prepared as described above, and 0.39 g (0.007 mole) of potassium hydroxide in 10 ml of absolute ethanol and 5 ml of water was stirred at room temperature for approximately 18 hours. The reaction mixture was concentrated, and water was added to the residue, forming a precipitate. The precipitate was collected on a filter paper and dried to give 0.79 g of (+)-4-phenyl-2-indanol, mp 87°–92° C., EE 50%.

EXAMPLE 2

Synthesis of (+)-4-Phenyl-2-Indanol

A. Hydroboration of 7-phenyl-1H-indene

This reaction was conducted in a manner similar to the procedure of Example 1A. A yield of 17.4 g of oily pot residue was obtained after Kugelrohr distillation of the product of the reaction of 32 g (0.23 mole) of (+)-α-pinene, 11 ml of a 1.05 M solution of borane-tetrahydrofuran complex (0.116 mole), 18.8 g (0.098 mole) of 7-phenyl-1H-indene, 40 ml of water, 60.3 ml of a 3 N aqueous solution of sodium hydroxide, 60.3 ml of a 30% aqueous solution of hydrogen peroxide, and 225 ml of tetrahydrofuran. Gas chromatographic analysis of the oil indicated it contained 37% 4-phenyl-2-indanol, 7% 4-phenyl-1-indanol and 55% unreacted 7-phenyl-1H-indene. Nuclear magnetic resonance analysis of the acetate derivatives of the mixture using a shift reagent, Eu(hfc)$_3$, showed a 41% EE of the dextrorotatory isomer for 4-phenyl-2-indanol.

B. Separation of 4-phenyl-2-indanol

Dehydration Method

A stirred solution of the product above, containing 4-phenyl-2-indanol, 4-phenyl-1-indanol, and 7-phenyl-1H-indene, and 0.05 g of p-toluenesulfonic acid monohydrate in 80 ml of toluene was heated at reflux for 5 minutes. The reaction mixture was cooled and applied to a column of silica gel. Elution was accomplished with toluene, then with 1:1 toluene/ethyl acetate to give, from appropriate fractions, 6.3 g (+)-4-phenyl-2-indanol, EE 48%.

EXAMPLE 3

Refinement of (+)-4-Phenyl-2-Indanol (+)-4-Phenyl-2-indanol (3.85 g, EE 48%) was finely powdered and added to 10 ml of toluene, and the mixture was stirred at room temperature for 1 hour. The insoluble material was collected on a filter paper and rinsed with a small amount (50 drops) of toluene. The collected material was dried to give 1.77 g of (+)-4-phenyl-2-indanol, mp 100°–101° C., EE 83%.

Several previously prepared samples of (+)-4-phenyl-2-indanol were combined to give 4.6 g, EE 57%. The combined sample was stirred in 15 ml of toluene at room temperature for 16 hours, and the insoluble material was collected to give 2.22 g of (+)-4-phenyl-2-indanol, mp 102°–103° C. This material was combined with 1.3 g of the EE 83% sample from above, and the process was repeated using 10 ml of toluene to give 2.9 g of (+)-4-phenyl-2-indanol, mp 102°–104° C., EE 92%.

In another run, 52.6 g of (+)-4-phenyl-2-indanol, EE 67%, gave, after successive washes with toluene, 30.4 g product, mp 103°–104° C., EE ≧ 95%, $[\alpha]_D^{24}$ +37.4°.

Example 4 illustrates the preparation of compounds of formula III.

EXAMPLE 4

Synthesis of Ethyl 3,3-Dimethyl-4,6,6-Trichloro-7,7,7-Trifluoroheptanoate

A stirred solution of 44.6 g (0.267 mole) of ethyl 3,3-dimethyl-4-pentenoate, 100 g (0.533 mole) of 1,1,1-trichlorotrifluoroethane, 0.27 g (0.0027 mole) of cuprous chloride, and 8.2 g (0.134 mole) of ethanolamine in 270 ml of tertiary butyl alcohol, under a nitrogen atmosphere, was heated at reflux for 16 hours. The reaction mixture was cooled to ambient temperature and extracted with three portions of 100 ml each of diethyl ether. A precipitate formed in the extracts, and was removed by vacuum filtration. The filter cake was washed with two portions of 25 ml each of diethyl ether. The ether extracts were combined with the washings, and the whole was concentrated under reduced pressure to an oily residue. Remaining volatile components were removed from the residue under further reduced pressure using a vacuum pump. The residue was subjected to distillation under reduced pressure to give 78.3 g of ethyl 3,3-dimethyl-4,6,6-trichloro-7,7,7-trifluoroheptanoate; bp 85°–87° at 0.12–0.15 mm. The nmr spectrum was consistent with the assigned structure.

Examples 5 and 6 illustrate preparation of the lower alkyl esters of formula IV. Example 5 is a two-step process via the intermediate of formula VII. Example 6 is a one-step process.

EXAMPLE 5

Synthesis of Methyl
(+)-Cis,Trans-3-(2-Chloro-3,3,3-Trifluoro-1-Propenyl)-2,2-Dimethylcyclopropanecarboxylate

A. Preparation of methyl (+)-cis,trans-3-(2,2-dichloro-3,3,3-trifluoropropyl)-2,2-dimethylcyclopropanecarboxylate A stirred solution of 37.0 g (0.112 mole) of methyl 3,3-dimethyl-4,6,6-trichloro-7,7,7-trifluoroheptanoate, 50 ml of tert-butyl alcohol, 50 ml of dimethylformamide, and 50 ml of hexane, under an argon atmosphere, was cooled to $-5°$ C. To the stirred solution was added dropwise a solution of 16.4 g (0.14 mole) of potassium tert-butoxide in 200 ml of tert-butyl alcohol at such a rate so as to maintain the reaction mixture temperature at $-3°$ to $-5°$ C. Upon complete addition, the reaction mixture was stirred for 4 hours at $-3°$ to $-5°$ C., then poured into a solution of 8.0 g of ammonium chloride in 250 ml of water. The mixture was extracted with two portions of 200 ml each of diethyl ether. The combined ether extracts were washed with two portions of 200 ml each of water. The ether layer was dried with sodium sulfate and filtered. The filtrate was evaporated under reduced pressure to a residual oil. The oil was distilled under reduced pressure to give 19.8 g of methyl (+)-cis,trans-3-(2,2-dichloro-3,3,3-trifluoropropyl)-2,2-dimethylcyclopropanecarboxylate; b.p. 55°–57° C./0.09 mm Hg. The ir and the nmr spectra were consistent with the proposed structure.

Analysis calc'd for $C_{10}H_{13}Cl_2F_3O_2$: C 40.98; H 4.47. Found: C 41.50; H 4.41.

B. Synthesis of methyl (+)-cis,trans-3-(2-chloro-3,3,3-trifluoro-1-propenyl)-2,2-dimethylcyclopropanecarboxylate A stirred solution of 30.6 g (0.105 mole) of methyl (±)-cis,trans-3-(2,2-dichloro-3,3,3-trifluoropropyl)-2,2-dimethylcyclopropanecarboxylate and 17.6 g (0.116 mole) of 1,5-diazabicyclo[5.4.0]undec-5-ene in 100 ml of dimethylformamide was heated at 100° C. for 4 hours. The reaction mixture was cooled and poured into a solution of 37.2 ml of concentrated hydrochloric acid in 300 ml of water. The mixture was extracted with three portions of 200 ml each of diethyl ether. The combined ether extracts were washed with an aqueous saturated solution of sodium chloride. The ether layer was dried with sodium sulfate and filtered. The filtrate was evaporated under reduced pressure to give a residual oil. The oil was dissolved in hexane, treated with decolorizing carbon, and filtered. The filtrate was evaporated under reduced pressure to a residual oil. The oil was distilled under reduced pressure to give in three fractions 10.0 g of methyl (+)-cis,trans-3-(2-chloro-3,3,3-trifluoro-1-propenyl)-2,2-dimethylcyclopropanecarboxylate; b.p. 40°–60° C./0.05 mm. The ir and the nmr spectra were consistent with the proposed structure. The nmr spectra indicated an 88:12 mixture of cis:trans isomers.

Analysis calc'd for $C_{10}H_{12}ClF_3O_2$: C 46.80; H 4.71. Found: C 46.91; H 4.79.

EXAMPLE 6

Synthesis of Ethyl
(+)-Cis,Trans-3-(2-Chloro-3,3,3-Trifluoro-1-Propenyl)-2,2-Dimethylcyclopropanecarboxylate To a stirred solution of 78.3 g (0.228 mole) of ethyl 3,3-dimethyl-4,6,6-trichloro-7,7,7-trifluoroheptanoate in 200 ml of distilled ethanol was added dropwise at ambient temperature 500 ml of an ethanolic solution of sodium ethoxide prepared from 11.5 g of metallic sodium (0.50 mole). After complete addition, the reaction mixture was stirred for one hour at ambient temperature, then allowed to stand for 18 hours. The cloudy reaction mixture was filtered and the filtrate evaporated under reduced pressure to give a residue. The residue was slurried in 200 ml of water, and the mixture was extracted with three portions of 50 ml each of diethyl ether. The combined extracts were dried with sodium sulfate and filtered. The filtrate was evaporated under reduced pressure to give, as a residual oil, 58.5 g of ethyl (+)-cis,trans-3-(2-chloro-3,3,3-trifluoro-1-propenyl)-2,2-dimethylcyclopropanecarboxylate. The nmr and ir spectra were consistent with the assigned structure and indicated the product was a mixture of approximately equal parts of cis and trans isomers.

Examples 7–9 illustrate preparation of the individual cis and trans isomers of the free acids of formula IV.

EXAMPLE 7

Synthesis of (±)-Trans- and
(+)-Cis,Trans-3-(2-Chloro-3,3,3-Trifluoro-1-Propenyl)-2,2-Dimethylcyclopropanecarboxylic Acid A solution of 16.2 g (0.06 mole) of ethyl (+)-cis,trans-3-(2-chloro-3,3,3-trifluoro-1-propenyl)-2,2-dimethylcyclopropanecarboxylate in 94 ml (0.078 mole) of a stock solution containing 3.34 g of sodium hydoxide, 94 ml of ethanol and 6 ml of water was stirred while heating under reflux for a period of 18 hours. The reaction mixture was concentrated under reduced pressure, 25 ml of water was added, and the mixture was acidified to pH 1 using 6 N hydrochloric acid. The acidified mixture was extracted with two portions of 50 ml each of diethyl ether. The combined extracts were dried with magnesium sulfate and filtered. The filtrate was evaporated under reduced pressure to give a residue. The residue was heated with 50 ml of hexane. The hot hexane was decanted from a tarry residue and cooled to yield a solid precipitate, which was collected by filtration, then dried to give 3.3 g of solid, m.p. 97°–103° C. Concentration of the mother liquor provided a second fraction of solid weighing 0.8 g, m.p. 96°–103° C. Nmr spectra of the two fractions indicated the solids were each (+)-trans-3-(2-chloro-3,3,3-trifluoro-1-propenyl)-2,2-dimethylcyclopropanecarboxylic acid. The mother liquor was evaporated to a residue. The residue was taken up in 50 ml of hexane and the solution cooled in a freezer for 18 hours. A solid precipitate was collected by filtration and dried to give 4.3 g of a solid, m.p. 64°–74° C. An nmr spectrum indicated the solid was a 50/50 mixture of cis and trans isomers of (+)-3-(2-chloro-3,3,3-trifluoro-1-propenyl)-2,2-dimethylcyclopropanecarboxylic acid.

EXAMPLE 8

Synthesis of (+)-Cis- and
(+)-Cis,Trans-3-(2-Chloro-3,3,3-Trifluoro-1-Propenyl)-2,2-Dimethylcyclopropanecarboxylic Acid A stirred solution of 90.0 g (0.35 mole) of methyl (+)-cis,trans-3-(2-chloro-3,3,3-trifluoro-1-propenyl)-2,2-dimethylcyclopropanecarboxylate (approximately 90% cis, prepared in accordance with Example 5B), 5.4 ml of concentrated sulfuric acid and 13.8 ml of water in 138 ml of acetic acid was heated under reflux for 1 hour. The reaction mixture was cooled and extracted with two portions of 100 ml each of diethyl ether. The combined extracts were dried with sodium sulfate, filtered, and the filtrate concentrated under reduced pressure to a solid residue. The residue was digested with 300 ml of hexane and the hexane solution was decanted from a dark, tarry residue and allowed to cool to ambient temperature. A solid precipitate formed and was collected by filtration to give 42.4 g of (+)-cis-3-(2-chloro-3,3,3-trifluoro-1-propenyl)-2,2-dimethylcyclopropanecarboxylic acid, as determined by nmr spectroscopy. A melting point was not determined. The melting point of another sample of cis acid prepared at a different time was 108°–110° C. The filtrate was concentrated and cooled to give 5.1 g of solid, identified by nmr spectroscopy to be a 50:50 mixture of (+)-cis,trans-3-(2-chloro-3,3,3-trifluoro-1-propenyl)-2,2-dimethylcyclopropanecarboxylic acid. The filtrate was cooled in dry ice to give an additional 8.1 g of a 50:50 mixture of the cis, trans isomers.

EXAMPLE 9

Synthesis of (+)-Cis-3-(2,2-Dibromoethenyl)-2,2-Dimethylcyclopropanecarboxylic Acid The starting material (+)-cis-3-(2,2-dichloroethenyl)-2,2-dimethylcyclopropanecarboxylic acid may be prepared by known methods such as that described in U.S. Pat. No. 4,024,163, to Elliott et al., May 17, 1977, at column 19, lines 45–61.

Under a dry nitrogen atmosphere, approximately 3 g of aluminum shot was added to 225 ml of dibromomethane. The temperature was raised to 35°–40° C., and hydrogen bromide gas was bubbled into the mixture. After 1 hour a reaction began to occur, and, with the temperature being maintained at 35°–40° C., a second and third portion of aluminum shot (total of 9.67 g, 0.358 mole) was added to the mixture. After complete addition, the reaction mixture was heated at 55° C. for 1 hour. The hydrogen bromide gas flow was stopped, and the reaction mixture was cooled to approximately 6° C. Cis-3-(2,2-dichloroethenyl)-2,2-dimethylcyclopropanecarboxylic acid (50.0 g, 0.239 mole) in 150 ml of dibromomethane was added to the cooled reaction mixture during 1 hour. After complete addition, the reaction mixture was stirred for 30 minutes. A nitrogen inlet was placed in the reaction mixture, and nitrogen was pulled through the mixture for 90 minutes by applying a slight vacuum to the reaction pot. Distilled water was added dropwise, and the resulting mixture was allowed to stand at room temperature for approximately 18 hours. The organic phase was separated, and the aqueous phase was extracted with 600 ml and 200 ml portions of diethyl ether. The ether washes were combined with the organic phase, and the whole was washed once with a 1 N hydrochloric acid solution and one with a saturated aqueous solution of sodium chloride. The organic phase was dried with magnesium sulfate, filtered, and the filtrate was concentrated under reduced pressure to give a solid. The solid was dried under a vacuum for 18 hours, then was crystallized twice from n-heptane and sublimed to give (+)-cis-3-(2,2-dibromoethenyl)-2,2-dimethylcyclopropanecarboxylic acid, m.p. 109°–111° C.

Examples 10 and 11 illustrate preparation of the acid halides of formula IV.

EXAMPLE 10

Synthesis of (+)-Trans-3-(2-Chloro-3,3,3-Trifluoro-1-Propenyl)-2,2-Dimethylcyclopropanecarbonyl Chloride To a stirred solution of 4.1 g (0.0173 mole) of (+)-trans-3-(2-chloro-3,3,3-trifluoro-1-propenyl)-2,2-dimethylcyclopropanecarboxylic acid in 40 ml of toluene at ambient temperature was added 1.7 g (0.022 mole) of pyridine, then 2.6 g (0.022 mole) of thionyl chloride in 25 ml of toluene. Upon complete addition the reaction mixture was stirred at ambient temperature for 17 hours. The reaction mixture was filtered through diatomaceous earth, and the filtrate was evaporated under reduced pressure to give 3.8 g of (+)-trans-3-(2-chloro-3,3,3-trifluoro-1-propenyl)-2,2-dimethylcyclopropanecarbonyl chloride. The ir spectrum was consistent with the assigned structure.

EXAMPLE 11

Synthesis of (+)-Cis-3-(2-Chloro-3,3,3-Trifluoro-1-Propenyl)-2,2-Dimethylcyclopropanecarbonyl Chloride A stirred solution of 10.0 g (0.04 mole) of (+)-cis-3-(2-chloro-3,3,3-trifluoro-1-propenyl)-2,2-dimethylcyclopropanecarboxylic acid in 100 ml of toluene was heated to 80° C. To this solution at 80° C. was added dropwise over 10 minutes a solution of 10.5 g (0.08 mole) of oxalyl chloride in 5 ml of toluene, and the whole heated at 80° C. for 26 hours. The toluene and excess oxalyl chloride were removed by distillation to give a residual oil which was distilled under reduced pressure using a Kugelrohr distilling system to give 8.2 g of (+)-cis-3-(2-chloro-3,3,3-trifluoro-1-propenyl)-2,2-dimethylcyclopropanecarbonyl chloride; b.p. 85° C./0.09 mm. The nmr and ir spectra were consistent with the proposed structure.

Examples 12–18 illustrate preparation of compounds of formula I wherein $R^2$ is other than hydrogen.

EXAMPLE 12

Synthesis of (+)-4-Phenyl-2-Indanyl (+)-Cis-3-(2-Chloro-3,3,3-Trifluoro-1-Propenyl)-2,2-Dimethylcyclopropanecarboxylate A. Use of 50% EE (+)-4-phenyl-2-indanol To a stirred solution of 0.3 g (0.0014 mole) of (+)-4-phenyl-2-indanol (EE 50%) and 0.13 g (0.0017 mole) of pyridine in 10 ml of toluene was added dropwise 0.36 g (0.0014 mole) of (+)-cis-3-(2-chloro-3,3,3-trifluoro-1-propenyl)-2,2-dimethylcyclopropanecarbonyl chloride in 5 ml of toluene, and the reaction mixture was stirred at room temperature for 18 hours. The reaction mixture was filtered to remove a precipitate, and the filtrate was concentrated under reduced pressure to give 0.63 g of an oily residue. The residue was subjected to column chromatography on silica gel, eluting first with hexane, then with 24:1 hexane/ethyl acetate to give (+)-4-phenyl-2-indanyl (+)-cis-3-(2-chloro-3,3,3-trifluoro-1-propenyl)-2,2-dimethylcyclopropanecarboxylate as an oil, EE 50% (alcohol moiety). The nmr spectrum was consistent with the proposed structure.

Analysis calc'd for $C_{24}H_{22}ClF_3O_2$: C 66.28; H 5.10. Found: C 65.57; H 5.41.

B. Use of ≧95% EE (+)-4-phenyl-2-indanol

In the manner of Example 12A, the reaction of 1.5 g (0.007 mole) of (+)-4-phenyl-2-indanol (EE≧95%) and 1.77 g (0.007 mole) of (+)-cis-3-(2-chloro-3,3,3-trifluoro-1-propenyl)-2,2-dimethylcyclopropanecarbonyl chloride in the presence of 0.7 g (0.009 mole) of pyridine and 20 ml of toluene gave 1.87 g of (+)-4-phenyl-2-indanyl (+)-cis-3-(2-chloro-3,3,3-trifluoro-1-propenyl)-2,2-dimethylcyclopropanecarboxylate as an oil, EE≧95% (alcohol moiety). The nmr spectrum was consistent with the proposed structure.

Analysis calc'd for $C_{24}H_{22}ClF_3O_2$: C 66.28, H 5.10. Found: C 66.40, H 5.11.

EXAMPLE 13

Synthesis of (+)-4-Phenyl-2-Indanyl 1R,Cis-3-(2,2-Dichloroethen-yl)-2,2-Dimethylcyclopropanecarboxylate A. Use of 50% EE (+)-4-phenyl-2-indanol 1R,cis-3-(2,2-Dichloroethenyl)-2,2-dimethylcyclopropanecarboxylic acid is the dextrorotatory isomer, i.e., (+)-cis, and may be prepared by known methods, for example, the method described in Example 32 of U.S. Pat. No. 4,024,163, issued to Elliott et al., May 17, 1977. This same method is also described by P. E. Burt et al. in *Pestic. Sci.* 5, 791 (1974), at Sections 2.3 and 2.4, pp 793 and 794.

Under a dry nitrogen atmosphere a stirred solution of 10.0 g (0.0478 mole) of 1R,cis-3-(2,2-dichloroethenyl)-2,2-dimethylcyclopropanecarboxylic acid in 50 ml toluene was heated to 78° C. Oxalyl chloride, 12.1 g (0.0957 mole), was added to the reaction mixture during 0.5 hour. After complete addition, the reaction mixture was stirred at 78° C. for approximately 65 hours, then cooled and concentrated under reduced pressure to give an oily residue. The residue was distilled under reduced pressure using a Kugelrohr distillation apparatus to give 10.2 g of 1R,cis-3-(2,2-dichloroethenyl)-2,2-dimethylcyclopropanecarbonyl chloride, b.p. 80° C./0.5 mm. The nmr spectrum was consistent with the proposed structure.

In a manner similar to Example 12A, the reaction of 0.32 g (0.0014 mole) of 1R,cis-3-(2,2-dichloroethenyl)-2,2-dimethylcyclopropanecarbonyl chloride with 0.3 g (0.0014 mole) of (+)-4-phenyl-2-indanol (EE 50%), 0.13 g (0.0017 mole) of pyridine, and toluene produced (+)-4-phenyl-2-indanyl 1R,cis-3-(2,2-dichloroethenyl)-2,2-dimethylcyclopropanecarboxylate as an oil, EE 50% (alcohol moiety). The nmr spectrum was consistent with the proposed structure.

B. Use of ≧95% EE (+)-4-phenyl-2-indanol

In the manner of Example 12A, the reaction of 1.5 g (0.007 mole) of (+)-4-phenyl-2-indanol (EE≧95%) and 1.26 g (0.006 mole) of 1R,cis-3-(2,2-dichloroethenyl)-2,2-dimethylcyclopropanecarbonyl chloride in the presence of 0.7 g (0.009 mole) of pyridine and 20 ml of toluene gave 1.59 g (+)-4-phenyl-2-indanyl 1R,cis-3-(2,2-dichloroethenyl)-2,2-dimethylcyclopropanecarboxylate as an oil, EE≧95% (alcohol moiety). The nmr spectrum was consistent with the proposed structure.

Analysis calc'd for $C_{23}H_{22}Cl_2O_2$: C 68.83, H 5.33. Found: C 68.72, H 5.47.

EXAMPLE 14

Synthesis of (+)-4-Phenyl-2-Indanyl (+)-Cis-3-(2,2-Dibromoethenyl)-2,2-Dimethylcyclopropanecarboxylate, EE 50% (Alcohol Moiety)

In a manner similar to Example 13A, the reaction of 13.0 g (0.0436 mole) of (+)-cis-3-(2,2-dibromoethenyl)-2,2-dimethylcyclopropanecarboxylic acid, 50 ml of toluene, and 11.1 g (0.0873 mole) of oxalyl chloride gave 7.0 g of (+)-cis-3-(2,2-dibromoethenyl)-2,2-dimethylcyclopropanecarbonyl chloride. The nmr spectrum was consistent with the proposed structure.

In a manner similar to Example 12A, the reaction of 0.51 g (0.0016 mole) of (+)-cis-3-(2,2-dibromoethenyl)-2,2-dimethylcyclopropanecarbonyl chloride (an additional four drops were added 1 hour after original addition) with 0.33 g (0.0016 mole) of (+)-4-phenyl-2-indanol (EE 50%), 0.16 g (0.002 mole) of pyridine and toluene produced an oil. The oil was subjected to vacuum column chromatography, whereby the oil was placed on silica gel packed in a sintered glass suction funnel, and the eluant was drawn through by water aspirator vacuum. Elution was accomplished with hexane, then 24:1 hexane/ethyl acetate to give (+)-4-phenyl-2-indanyl (+)-cis-3-(2,2-dibromoethenyl)-2,2-dimethylcyclopropanecarboxylate as an oil, EE 50% (alcohol moiety). The nmr spectrum was consistent with the proposed structure.

Analysis calc'd for $C_{23}H_{22}Br_2O_2$: C 56.35; H 4.52. Found: C 57.40; H 4.76.

EXAMPLE 15

Synthesis of (+)-4-Phenyl-2-Indanyl (+)-Cis,Trans-3-(2,2-Dichloroethenyl)-2,2-Dimethylcyclopropanecarboxylate, EE 50% (Alcohol Moiety), Cis/Trans 80:20

Under a dry nitrogen atmosphere, a stirred solution of 50.0 g (0.239 mole) of (+)-cis-3-(2,2-dichloroethenyl)-2,2-dimethylcyclopropanecarboxylic acid in 130 ml of dry toluene was warmed to 80° C. A solution of 60.67 g (0.478 mole) of oxalyl chloride in 30 ml of toluene was added dropwise to the reaction mixture during 1 hour. The reaction mixture was heated at 100° C. for 16 hours, then cooled and concentrated under reduced pressure to give an oil. The oil was distilled using a Kugelrohr distillation apparatus (65° C./0.025 mm) to give 45.6 g of (+)-cis,trans-3-(2,2-dichloroethenyl)-2,2-dimethylcyclopropanecarbonyl chloride, b.p. 65° C./0.025 mm. The nmr spectrum indicated the product was an 80:20 mixture of the cis and trans isomers.

In a manner similar to Example 12A, the reaction of 0.36 g (0.0016 mole) of (+)-cis,trans-3-(2,2-dichloroethenyl)-2,2-dimethylcyclopropanecarbonyl chloride (an additional four drops were added 4 hours after original addition) with 0.33 g (0.0016 mole) of (+)-4-phenyl-2-indanol (EE 50%), 0.16 g (0.002 mole) of pyridine and toluene gave an oil. The oil was subjected to vacuum column chromatography on silica gel (see Example 14), eluting first with hexane then with 24:1 hexane/ethyl acetate, to given an oil. The oil was rechromatographed as described above to give (+)-4-phenyl-2-indanyl (+)-cis,trans-3-(2,2-dichloroethenyl)-2,2-dimethylcyclopropanecarboxylate as an oil, EE 50% (alcohol moiety), cis/trans 80:20. The nmr and ir spectra were consistent with the proposed structure.

Analysis calc'd for $C_{23}H_{22}Cl_2O_2$: C 68.83; H 5.53. Found: C 68.97; H 5.68.

EXAMPLE 16

Synthesis of (+)-4-Phenyl-2-Indanyl (+)-Trans-3-(2,2-Dichloroethenyl)-2,2-Dimethylcyclopropanecarboxylate, EE 50% (Alcohol Moiety)

(+)-trans-3-(2,2-Dichloroethenyl)-2,2-dimethylcyclopropanecarboxylic acid may be prepared by known methods, for example, the method described in U.S. Pat. No. 4,024,163, to Elliott et al., May 17, 1977, at column 19, lines 45-61.

In a manner similar to Example 13A, the reaction of 25.0 g (0.12 mole) of (+)-trans-3-(2,2-dichloroethenyl)-2,2-dimethylcyclopropanecarboxylic acid, 180 ml of toluene, and 30.4 g (0.24 mole) of oxalyl chloride gave 25.8 g of (+)-trans-3-(2,2-dichloroethenyl)-2,2-dimethylcyclopropanecarbonyl chloride. The nmr spectrum was consistent with the proposed structure.

In a manner similar to Example 12A, the reaction of 0.41 g (0.0018 mole) of (+)-trans-3-(2,2-dichloroethenyl)-2,2-dimethylcyclopropanecarbonyl chloride with 0.37 g (0.0018 mole) of (+)-4-phenyl-2-indanol (EE 50%), 0.16 g (0.002 mole) of pyridine and toluene gave (+)-4-phenyl-2-indanyl (+)-trans-3-(2,2-dichloroethenyl)-2,2-dimethylcyclopropanecarboxylate, EE 50% (alcohol moiety). The nmr and ir spectra were consistent with the proposed structure.

Analysis calc'd for $C_{23}H_{22}Cl_2O_2$: C 68.83; H 5.53. Found: C 68.82; H 5.36.

EXAMPLE 17

Synthesis of (+)-4-Phenyl-2-Indanyl (+)-Cis-3-(2,2-Dichloroethenyl)-2,2-Dimethylcyclopropanecarboxylate, EE≧95% (Alcohol Moiety)

(+)-cis-3-(2,2-Dichloroethenyl)-2,2-dimethylcyclopropanecarboxylic acid may be prepared by known methods, for example, the method described in U.S. Pat. No. 4,024,163, to Elliott et al., May 17, 1977, at column 19, lines 45-61. The corresponding acid chloride may be prepared by the method described in Example 13A above.

In a manner similar to Example 12A, the reaction of 1.54 g (0.007 mole) of (+)-cis-3-(2,2-dichloroethenyl)-2,2-dimethyl-cyclopropanecarbonyl chloride and 1.5 g (0.007 mole) of (+)-4-phenyl-2-indanol (EE≧95%) in the presence of 0.7 g (0.009 mole) of pyridine and 20 ml of toluene gave 1.84 g of (+)-4-phenyl-2-indanyl (+)-cis-3-(2,2-dichloroethenyl)-2,2-dimethylcyclopropanecarboxylate as an oil, EE≧95% (alcohol moiety). The nmr spectrum was consistent with the proposed structure.

Analysis calc'd for $C_{23}H_{22}Cl_2O_2$: C 68.83, H 5.53. Found: C 68.89, H 5.32.

EXAMPLE 18

Synthesis of (+)-4-Phenyl-2-Indanyl 2,2,3,3-Tetramethylcyclopropanecarboxylate, EE≧95%

2,2,3,3-Tetramethylcyclopropanecarboxylic acid may be prepared by known methods, for example, the method in *Synthetic Pyrethroids*, ACS Symposium Series, No. 42, M. Elliott, Ed., American Chemical Society, Washington, D.C., 1977, Chapter 4, FIG. 4, page 48 and accompanying text. The corresponding acid chloride may be prepared by the method described in Example 13A above.

In a manner similar to Example 12A, the reaction of 1.09 g (0.007 mole) of 2,2,3,3-tetramethylcyclopropanecarbonyl chloride and 1.5 g (0.007 mole) of (+)-4-phenyl-2-indanol (EE≧95%) in the presence of 0.7 g (0.009 mole) of pyridine and 20 ml of toluene gave 1.48 g of (+)-4-phenyl-2-indanyl 2,2,3,3-tetramethylcyclopropanecarboxylate, EE≧95%. The nmr spectrum was consistent with the proposed structure.

Analysis calc'd for $C_{23}H_{26}O_2$: C 82.60, H 7.84. Found: C 82.88, H 7.93.

In the method aspect of this invention, an effective insecticidal or acaricidal amount of the compound of formula I wherein $R^2$ is other than hydrogen is applied to the locus where control is desired, i.e., to the insect or acarid itself or to the foliage or seeds of agricultural plants. The compounds are useful for the control household, veterinary, and crop pests of the phylum Arthropoda, and may be applied as technical material or as formulated product. Typical formulations include compositions of the active ingredient in combination with an agriculturally acceptable carrier or extender, preferably with a surface active agent, and optionally with other active ingredient. Suitable formulations include granules, powders, or liquids, the choice varying with the type of pest and environmental factors present at the particular locus of infestation. Thus, the compounds may be formulated as granules of various sizes, as dusts, as wettable powders, as emulsifiable concentrates, as solutions, as dispersions, as controlled release compositions, and the like. A typical formulation may vary widely in concentration of active ingredient depending upon the particular agent used, the additives and carriers used, other active ingredients, and the desired mode of application. With due consideration to these factors the active ingredient of a typical formulation may, for example, be suitably present at a concentration of about 0.01% up to about 99.5%, preferably 0.1% up to 90% or 95%, of the formulation. An agriculturally acceptable carrier may comprise about 99.5% by weight to as low as about 0.5% by weight of the formulation. Compatible surface active agents, if employed in a formulation, may be present at various concentrations, suitably in the range of 1 to 30% by weight of the formulation.

The formulation may be used as such or diluted to a desired use dilution with a diluent or carrier suitable for facilitating dispersion of the active ingredients. A concentration of the active ingredient in the use dilution may be in the range of 0.001% to about 50%, preferably up to about 10% by weight.

Many variations of spraying, dusting, and controlled or slow release compositions of a type known in the art may be used by substituting or adding an insecticidal compound or compounds of this invention into the compositions known or apparent to the art.

The insecticidal or acaricidal compounds of this invention may be formulated and applied with other compatible active agents including nematicides, insecticides, acaricides, fungicides, plant regulators, herbicides, fertilizers, and the like.

In applying these compounds, whether alone or with other agricultural chemicals, an effective insecticidal or acaricidal amount of the active ingredient must be applied. While the application rate will vary widely depending on the choice of compound, formulation, mode of application, plant species being protected, planting density and other like factors, a suitable use rate for agricultural crops may be in the range of 0.005 to 3 k/ha, preferably 0.01 toabout 1 k/ha.

The insecticidal or acaricidal compounds of this invention were tested for pesticidal activity as described in Examples 19-21 below.

EXAMPLE 19

Foliar Application Test

The test compound was dissolved in 5-10 ml of acetone containing 0.25% octylphenoxypolyethoxyethanol. This solution was dispersed in a solution of 90% water, 9.75% acetone, and 0.25% octylphenoxypolyethoxyethanol to give a solution having 512 ppm (w/w) active ingredient. Aliquots of this solution were diluted with an appropriate amount of water to provide solutions containing various concentrations of active ingredient. Test organisms and techniques were as follows: The activity against Mexican bean beetle (*Epilachna varivestis* Muls.) and southern armyworm (*Spodoptera eridania* [Cram.]) was evaluated by spraying the leaves of pinto bean plants with the test solution and infesting with 3rd instar larvae after the foliage had dried. The activity against the pea aphid (*Acrythosiphon pisum* [Harris]) was evaluated on broad bean plants whose leaves were sprayed before infestation with adult aphids. The activity against twospotted spider mites (*Tetranychus urticae* [Koch]) was evaluated on pinto bean plants the leaves of which were dipped or sprayed with test solution after infestation with adult mites. To prevent escape of the insects from the test site, the complete test plant or the incised leaves were placed in capped paper cups. The tests were transferred to a holding room at 80° C. and 50% relative humidity for an exposure period of at least 48 hours. At the end of this time the dead and living insects were counted and the percent kill was calculated. Results of these tests are summarized in the table below. The results indicated generally a high level of activity against both insects and mites. Data from lower dosing rates, not shown in the table below, indicate a particularly high susceptibility of the beetles to the present compounds.

| | Activity In Foliar Application Test | | | | |
|---|---|---|---|---|---|
| Compound | Conc. | Percent Kill | | | |
| of Example | (ppm) | SAW | MBB | PA | TSM |
| 12A | 64 | 100 | 100 | 90 | 98 |
|  | 16 | 100 | 100 | 90 | 89 |
| 12B | 64 | 100 | 100 | — | 100 |
|  | 16 | 100 | 100 | — | 100 |
| 13A | 64 | 100 | 100 | 100 | 100 |
|  | 16 | 100 | 100 | 85 | 96 |
| 13B | 64 | 100 | 100 | — | 100 |
|  | 16 | 100 | 100 | — | 100 |
| 14 | 64 | 100 | 100 | 100 | 100 |
|  | 16 | 95 | 100 | 100 | 17 |
| 15 | 64 | 95 | 100 | 100 | 100 |
|  | 16 | 95 | 95 | 100 | 100 |
| 16 | 64 | 100 | 100 | 100 | — |
|  | 16 | 100 | 70 | 90 | — |
| 17 | 64 | 100 | 100 | — | — |
|  | 16 | 100 | 100 | — | — |
| 18 | 64 | 100 | 85 | — | — |
|  | 16 | 85 | 75 | — | — |

SAW—southern armyworm
MBB—Mexican bean beetle
PA—pea aphid
TSM—twospotted spider mite

EXAMPLE 20

Topical Application Test

Two replicates of ten larvae of each test species were employed for each test compound. A 9 cm petri dish lined with a piece of filter paper, and containing a food source was employed for each replicate. A one microliter droplet of a 5 mg/ml solution of test compound in acetone, a dosing rate equivalent to 5000 nanograms/insect, was applied to the second or third dorsal thoracic segment of each larva. The tests were read twenty-four hours after application of the toxicant solution, and the percent kill was determined. The insects employed were southern armyworm (*Spodoptera eridania* [Cram.]), Mexican bean beetle (*Epilachna varivestis* Muls.), and milkweed bug (*Oncopeltus faciatus* [Dallas]). All the exemplified compounds, the compounds of Examples 12A-18, exhibited 100% control for each test species under the above conditions.

EXAMPLE 21

Comparative Activity

Compounds of the present invention which have an enantiomeric excess of the dextrorotatory isomer of the alcohol moiety were compared in both foliar and topical application tests with the corresponding compounds bearing a racemic alcohol moiety. The tests were conducted in accordance with the procedures set forth above in Examples 19 and 20 with the exception that various dosing rates to obtain LD$_{50}$ values were employed, and additional insect species were used. Relative potency, based on a value of 1.0 for each compound having a racemic alcohol moiety, was determined by comparing the LD$_{50}$ for the test compound with that for the standard. The insect species were southern armyworm (*Spodoptera eridania* [Cram.]), cabbage looper (*Trichoplusia ni* [Hubner]), tobacco budworm (*Heliothis virescens* [Fabricius]), Mexican bean beetle (*Epilachna varivestis* Muls.), milkweed bug (*Oncopeltus faciatus* [Dallas]), and pea aphid (*Acyrothosiphon pisum* [Harris]), identified respectively in the tables below as SAW, CL, TBW, MBB, MWB, and PA. With certain exceptions, the present compounds exhibited higher activity than the corresponding compounds having a racemic alcohol moiety.

Comparative Activity
Foliar Application Test

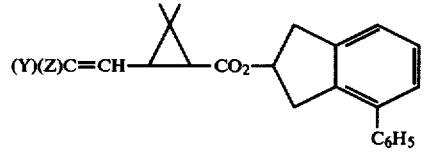

| Cpd of Example | Y | Z | Alcohol Moiety | Acid Moiety | Relative Potency | | |
|---|---|---|---|---|---|---|---|
| | | | | | SAW | MBB | PA |
| — | Cl | CF$_3$ | racemic | (+)-cis | 1.0 | 1.0 | 1.0 |
| 12A | Cl | CF$_3$ | (+), EE 50% | (+)-cis | 1.4 | 2.0 | 0.6 |
| 12B | Cl | CF$_3$ | (+), EE ≧95% | (+)-cis | 1.3 | 2.0 | 1.5 |
| — | Cl | Cl | racemic | 1R,cis | 1.0 | 1.0 | 1.0 |
| 13A | Cl | Cl | (+), EE 50% | 1R,cis | 1.6 | 2.8 | 0.5 |
| 13B | Cl | Cl | (+), EE ≧95% | 1R,cis | 1.3 | 1.3 | 0.9 |

-continued

**Comparative Activity
Foliar Application Test**

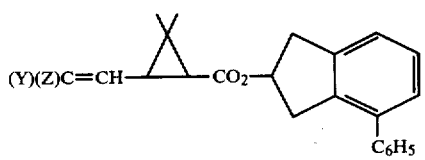

| Cpd of Example | Y | Z | Alcohol Moiety | Acid Moiety | Relative Potency | | |
|---|---|---|---|---|---|---|---|
| | | | | | SAW | MBB | PA |
| — | Cl | Cl | racemic | (+)-trans | 1.0 | 1.0 | 1.0 |
| 16 | Cl | Cl | (+), EE 50% | (+)-trans | 1.2 | 1.2 | 1.7 |

-continued

**Comparative Activity
Foliar Application Test**

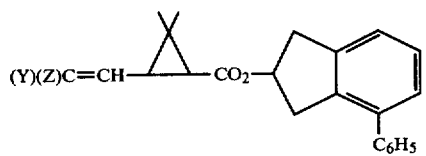

| Cpd of Example | Y | Z | Alcohol Moiety | Acid Moiety | Relative Potency | | |
|---|---|---|---|---|---|---|---|
| | | | | | SAW | MBB | PA |
| | | | EE ≧95% | | | | |

**Comparative Activity
Topical Application Test**

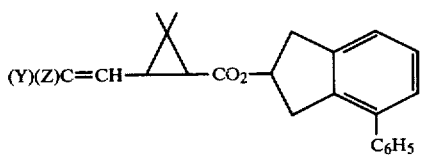

| Cpd of Example | Y | Z | Alcohol Moiety | Acid Moiety | Relative Potency | | | | |
|---|---|---|---|---|---|---|---|---|---|
| | | | | | SAW | MBB | MWB | TBW | CL |
| — | Cl | CF$_3$ | racemic | (+)-cis | 1.0 | 1.0 | 1.0 | 1.0 | 1.0 |
| 12A | Cl | CF$_3$ | (+), EE 50% | (+)-cis | 2.3 | 3.2 | 1.6 | 1.7 | 1.1 |
| 12B | Cl | CF$_3$ | (+), EE ≧95% | (+)-cis | 2.3 | 1.4 | 7.0 | 2.4 | 2.3 |
| — | Cl | Cl | racemic | 1R,cis | 1.0 | 1.0 | 1.0 | 1.0 | 1.0 |
| 13A | Cl | Cl | (+), EE 50% | 1R,cis | 2.3 | 1.9 | 2.9 | 1.0 | 1.7 |
| 13B | Cl | Cl | (+), EE ≧95% | 1R,cis | 3.1 | 1.2 | 5.1 | 1.3 | 2.1 |
| — | Br | Br | racemic | (+)-cis | 1.0 | 1.0 | 1.0 | — | 1.0 |
| 14 | Br | Br | (+), EE 50% | (+)-cis | 3.0 | 1.7 | 7.4 | — | 1.8 |
| — | Cl | Cl | racemic | (+)-trans | 1.0 | 1.0 | 1.0 | — | 1.0 |
| 16 | Cl | Cl | (+), EE 50% | (+)-trans | 2.0 | 0.9 | 5.8 | — | 0.7 |
| — | Cl | Cl | racemic | (+)-cis | 1.0 | 1.0 | 1.0 | 1.0 | 1.0 |
| 17 | Cl | Cl | (+), EE ≧95% | (+)-cis | 2.3 | 1.1 | 1.9 | 2.3 | 2.9 |
| — | Cl | Cl | racemic | (+)-cis | 1.0 | 1.0 | 1.0 | | |
| 17 | Cl | Cl | (+), | (+)-cis | 1.1 | 1.1 | 0.3 | | |

I claim:
1. A 4-substituted-2-indanyl compound of the formula

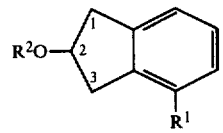

wherein R$^1$ is phenyl which may be substituted with halogen or lower alkyl, R$^2$ is hydrogen, and the isomer of S configuration at C-2 of the indanyl ring is present in an enantiomeric excess of at least 25% over the isomer of R configuration at C-2 of the indanyl ring.

2. The compound of claim 1 wherein R$^1$ is phenyl.

3. The compound of claim 2 wherein the enantiomeric excess of the 2S isomer is at least 60%.

* * * * *